United States Patent
Kato et al.

(10) Patent No.: US 10,532,201 B2
(45) Date of Patent: Jan. 14, 2020

(54) DRUG ADMINISTRATION DEVICE, AND MANUFACTURING METHOD FOR DRUG ADMINISTRATION DEVICE

(71) Applicants: TOPPAN PRINTING CO., LTD., Tokyo (JP); JAPAN AS REPRESENTED BY DIRECTOR-GENERAL OF NAT'L INST. OF INFECTIOUS DISEASES, Tokyo (JP)

(72) Inventors: Hiroyuki Kato, Tokyo (JP); Tomoya Sumida, Tokyo (JP); Yoshihiro Kodama, Tokyo (JP); Seishiro Naito, Tokyo (JP)

(73) Assignees: TOPPAN PRINTING CO., LTD., Tokyo (JP); JAPAN AS REPRESENTED BY DIRECTOR-GENERAL OF NATIONAL INSTITUTE OF INFECTIOUS DISEASES, Tokyo (JP)

( * ) Notice: Subject to any disclaimer, the term of this patent is extended or adjusted under 35 U.S.C. 154(b) by 0 days.

(21) Appl. No.: 15/701,216

(22) Filed: Sep. 11, 2017

(65) Prior Publication Data
US 2017/0368322 A1 Dec. 28, 2017

Related U.S. Application Data

(63) Continuation of application No. PCT/JP2015/081847, filed on Nov. 12, 2015.

(30) Foreign Application Priority Data

Mar. 18, 2015 (JP) ................................. 2015-054687

(51) Int. Cl.
*A61M 37/00* (2006.01)

(52) U.S. Cl.
CPC . *A61M 37/0015* (2013.01); *A61M 2037/0053* (2013.01)

(58) Field of Classification Search
CPC .............. A61M 37/0015; A61M 37/00; A61M 2037/003; A61M 2037/0053;
(Continued)

(56) References Cited

U.S. PATENT DOCUMENTS 6,132,755 A * 10/2000 Eicher ................. A61M 31/002
424/427
6,890,319 B1 * 5/2005 Crocker ............... A01K 11/005
604/131
(Continued)

FOREIGN PATENT DOCUMENTS

DE   10 2008 052 749 A1   5/2010
EP         3135334 A4 *    6/2017
(Continued)

OTHER PUBLICATIONS

Extended European Search Report dated Nov. 14, 2018, in European Patent Application No. 15885568.4, 6 pages.
(Continued)

*Primary Examiner* — Nathan R Price
*Assistant Examiner* — Mark Alan Igel
(74) *Attorney, Agent, or Firm* — Squire Patton Boggs (US) LLP

(57) ABSTRACT

A drug administration device includes a substrate having a first surface, a projection extending from the first surface, and a solid drug. One direction that intersects with the first surface is a first direction, and one direction that extends along the first surface is a second direction. A groove serving as a receiving section is formed in the projection. The groove defines a cavity recessed in the first direction toward the substrate and extends in the second direction to open to a (Continued)

section of the peripheral surface of the projection. The drug is received in the groove.

6 Claims, 8 Drawing Sheets

(58) Field of Classification Search
CPC .. A61M 2037/0046; A61M 2037/0038; A61M 2202/30; A61B 5/150984; A61B 17/30
See application file for complete search history.

(56) References Cited

U.S. PATENT DOCUMENTS

| | | | |
|---|---|---|---|
| 2002/0177858 A1* | 11/2002 | Sherman | A45D 26/0004 606/131 |
| 2002/0183688 A1* | 12/2002 | Lastovich | A61B 17/205 604/27 |
| 2003/0009113 A1* | 1/2003 | Olson | A61B 5/14532 600/573 |
| 2006/0051404 A1* | 3/2006 | Yeshurun | A61B 17/205 424/449 |
| 2007/0066934 A1* | 3/2007 | Etheredge, III | A61B 17/205 604/46 |
| 2008/0125743 A1* | 5/2008 | Yuzhakov | A61M 37/0015 604/506 |
| 2009/0131887 A1* | 5/2009 | Shiomitsu | A61M 37/0015 604/272 |
| 2009/0200262 A1* | 8/2009 | Scholten | A61M 37/0015 216/11 |
| 2010/0305516 A1* | 12/2010 | Xu | A61M 37/0015 604/272 |
| 2012/0296280 A1* | 11/2012 | Eum | A61M 37/0015 604/113 |
| 2014/0066864 A1 | 3/2014 | Eum | |
| 2014/0259652 A1* | 9/2014 | Pushpala | G01N 27/3271 29/825 |
| 2017/0080613 A1* | 3/2017 | Asai | B29C 43/56 |

FOREIGN PATENT DOCUMENTS

| | | |
|---|---|---|
| JP | 2005-246595 A | 9/2005 |
| JP | 2006-516201 | 6/2006 |
| JP | 2006-341089 A | 12/2006 |
| JP | 2007-260889 A | 10/2007 |
| JP | 2013-517889 A | 5/2013 |
| JP | 2013-252580 A | 12/2013 |
| WO | WO 2014/105458 A1 | 7/2014 |

OTHER PUBLICATIONS

International Preliminary Report on Patentability dated Sep. 19, 2017, in International Patent Application No. PCT/JP2015/081847, 5 pages.
Notice of Reasons for Refusal dated Jul. 9, 2019, in Japanese Patent Application No. 2017-506018, 8 pages.

* cited by examiner

DRUG ADMINISTRATION DEVICE, AND MANUFACTURING METHOD FOR DRUG ADMINISTRATION DEVICE

BACKGROUND

The present disclosure relates to a drug administration device, such as a microneedle device for administering a drug, and a method for manufacturing the drug administration device.

Microneedle devices are known drug administration devices for transdermal or intradermal administration of drugs. A microneedle device includes a plurality of needle-shaped projections provided on the surface of a substrate. To administer a drug using the microneedle device, the substrate is pressed onto the skin so that the projections pierce the skin. The pores created by the projections allow the drug to be delivered into the body (See Japanese Laid-Open Patent Publication No. 2006-341089, for example).

A microneedle device including a drug is formed for example by applying a liquid drug to the surface of projections around the tips and then drying the drug. However, when the amount of drug applied to the projections in such a structure equals or exceeds a certain level, the drug will form a spherical shape and solidify around the tips of the projections, lowering the piercing ability of the projections. This places a significant limit on the amount of drug applied and therefore on the amount of drug to be administered using the microneedle device.

SUMMARY

To solve the problem described above, it is an objective of the present disclosure to provide a drug administration device that holds a greater amount of drug and a method for manufacturing the drug administration device.

To achieve the foregoing objective and in accordance with one aspect of the present disclosure, a drug administration device is provided that includes a substrate having a first surface, a projection extending from the first surface and including a peripheral surface, and a solid drug. One direction that intersects with the first surface is a first direction. One direction that extends along the first surface is a second direction. The projection includes a receiving section. The receiving section defines a cavity recessed in the first direction toward the substrate and extends in the second direction to open to a section of the peripheral surface of the projection. The drug is received in the receiving section.

The drug is received in the receiving section, which is recessed inward of the projection. This increases the amount of drug the drug administration device can hold as compared with a structure in which the drug is adhered to the surface of the projection.

In the above-described configuration, the drug is preferably a freeze-dried drug.

The drug administration device that includes the freeze-dried drug can be stored for a long time.

In the above-described configuration, the receiving section preferably extends through the projection in the second direction.

This facilitates the entry of drug into the receiving section and thus the loading of drug.

In the above-described configuration, the receiving section is preferably a groove having a bottom, and the bottom of the groove is preferably located at a position separated from the substrate in the first direction.

This increases the mechanical strength of the projection at the base of the projection where stress tends to be concentrated, as compared with a structure in which the bottom of the groove is in the substrate. Moreover, the drug is concentrated in the part of the projection that goes deeper into the skin than the other part. This facilitates the delivery of the drug from the groove into the body of the administration subject.

In the above-described configuration, the projection preferably includes a pointed distal end having an apex, and as viewed facing the first surface, the apex is preferably located in an edge of the projection.

The pointed distal end of the projection easily pierces the skin. In addition, the tip of the projection is located in an edge of the projection, increasing the flexibility in the size, shape, and position of the receiving section, which is positioned in a region that does not include the tip.

In the above-described configuration, the projection is preferably one of a plurality of projections, and all of the projections preferably have the same second direction.

The receiving sections of the projections are formed in the same direction. Thus, the receiving sections may be formed simultaneously in the projections, or a receiving section may be formed successively in each of the projections using various processing techniques, such as machining or laser processing. This enhances the production efficiency of the drug administration device.

To achieve the foregoing objective and in accordance with one aspect of the present disclosure, a method for manufacturing a drug administration device is provided. The method includes a first step of fabricating a main body, wherein the main body includes a substrate, which includes a first surface, and a projection, which extends from the first surface and has a peripheral surface and a receiving section, a second step of loading a liquid drug into the receiving section, and a third step of drying the drug loaded in the receiving section. One direction that intersects with the first surface is a first direction. One direction that extends along the first surface is a second direction. The receiving section defines a cavity recessed in the first direction toward the substrate and extends in the second direction to open to a section of the peripheral surface of the projection.

The method allows for manufacturing the drug administration device that holds a greater amount of drug as described above.

In the above-described method, the third step preferably includes freeze-drying the drug.

The method freeze-dries the drug, enabling the drug administration device to be stored for a long time.

DESCRIPTION OF EXEMPLARY EMBODIMENTS

Referring to FIGS. 1 to 7, a drug administration device and a method for manufacturing the drug administration device according to one embodiment will be described. In this embodiment, the drug administration device is a microneedle device.

[Structure of Microneedle device] Referring to FIGS. 1 to 3, the structure of the microneedle device will now be described.

Figure 1:
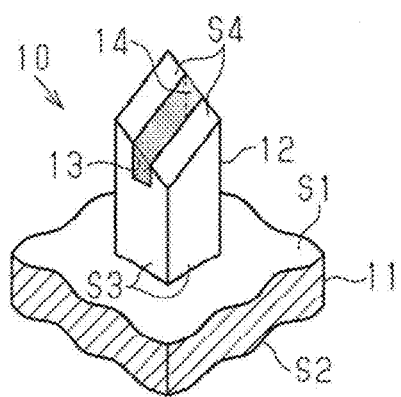
FIG. 1 is a perspective view showing the perspective structure of a microneedle device, which is an example of a drug administration device according to one embodiment.

As shown in FIG. 1, a microneedle device 10 includes a planar substrate 11, a projection 12 extending from the substrate 11, and a freeze-dried drug 14, which is received in a groove 13. The groove 13 is an example of the receiving section. The substrate 11 includes a first surface S1, on which the projection 12 is formed, and a second surface S2, which is opposite to the first surface S1. The first surface S1 supports the base of the projection 12.

In the example shown in FIG. 1, the structure formed by the projection 12 and the freeze-dried drug 14 has the shape of a rectangular prism that is beveled relative to the extending direction of the rectangular prism. The projection 12 includes side surfaces S3, which are peripheral surfaces extending perpendicularly from the rectangle base surface defined in the first surface S1, and an upper surface S4, which is inclined relative to the base surface. All sides of the upper surface S4 are inclined relative to the base surface. The length of the projection 12 from the first surface S1 is the greatest at the apex of the upper surface S4, which is located on the farther side from the viewer of FIG. 1.

The projection 12 includes a groove 13, which extends in a direction perpendicular to the first surface S1, extends along one of the two pairs of opposing sides defining the base surface of the projection 12, and extends through the projection 12 in a direction along the first surface S1. That is, the groove 13 opens to the upper surface S4 and extends across the upper surface S4. In the present embodiment, the direction perpendicular to the first surface S1 is an example of the first direction, and the direction extending along the first surface S1 and along specific one of the two pairs of opposing sides defining the base surface of the projection 12 is an example of the second direction.

In other words, the groove 13 defines a cavity recessed in the first direction toward the substrate 11. The cavity extends continuously in the second direction so that the groove 13 opens to sections of side surfaces S3. More specifically, the groove 13 opens to the upper surface S4 and two sections of side surfaces S3 of the projection 12 so as to form a continuous opening.

The groove 13 receives the freeze-dried drug 14, which is a drug that is freeze-dried. In this structure, the freeze-dried drug 14 is exposed to the surface of the microneedle device 10 as viewed facing the first surface S1. The freeze-dried drug 14 is also exposed to a surface of the microneedle device 10 as viewed in a direction parallel to the first surface S1.

Figure 2:
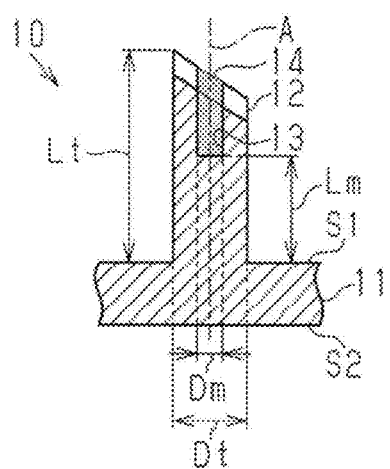
FIG. 2 is a cross-sectional view showing the cross-sectional structure of the microneedle device of the embodiment.

As shown in FIG. 2, the bottom of the groove 13 is located in the projection 12 at a position separated from the substrate 11 in the direction perpendicular to the first surface S1.

The projection 12 has a length Lt that is measured from the first surface S1 of the substrate 11 to the tip of the projection 12 in the direction perpendicular to the first surface S1. The length Lt of the projection 12 may be set depending on factors such as the purpose of piercing by the projection 12 or the type of the drug to be administered. For example, the length Lt of the projection 12 is set such that, when the projection 12 pierces the human skin, the tip of the projection 12 extends beyond the stratum corneum, which is the outermost layer of the skin, but does not reach the nerve layer. Such a length Lt of the projection 12 is preferably between 100 μm and 2 mm. Further, the maximum width Dt of the projection 12 in the direction along the first surface S1 and as viewed in a direction along the extending direction of the groove 13, that is, the maximum width Dt of the projection 12 as viewed in the second direction, is preferably between 10 μm and 600 μm.

The size of the groove 13 may be set depending on the intended dosage of the drug and within the range that does not excessively lower the mechanical strength of the projection 12. The width Dm of the groove 13 as viewed in the second direction may be about ⅕ to ½ of the width Dt of the projection 12. The width Dm that is less than ⅕ of the width Dt provides a sufficient mechanical strength of the projection 12. However, the loading of the drug in the groove 13 will be difficult, and the amount of drug that can be loaded into the groove 13 will be reduced. The width Dm that is greater than ½ of the width Dt allows the groove 13 to receive a greater amount of drug but weakens the mechanical strength of the projection 12. When the width Dm varies, the maximum value of the width Dm is preferably greater than or equal to ⅕ of the width Dt, and the minimum value of the width Dm is preferably less than or equal to ½ of the width Dt.

The length Lm that is measured from the first surface S1 to the bottom of the groove 13 in the direction perpendicular to the first surface S1 is preferably about ⅓ or more of the length Lt of the projection 12. The length Lm that is greater than or equal to ⅓ of the length Lt facilitates the delivery of the freeze-dried drug 14 from the groove 13 into the body. The length Lm is preferably about less than or equal to ⅘ of the length Lt. The length Lm that is less than or equal to ⅘ of the length Lt allows for the formation of a coagulated mass of a sufficient size when the liquid drug loaded in the groove 13 is freeze-dried and coagulated. This increases the likelihood that the freeze-dried drug is held in the groove 13.

The projection 12 has a pointed distal end. The tip, which is the apex of the distal end, is offset from a straight line A that extends in the extending direction of the projection 12 and passes through the center of the base surface of the projection 12. The tip of the projection 12 is located in an edge of the projection 12 as viewed facing the first surface S1.

Figure 3:
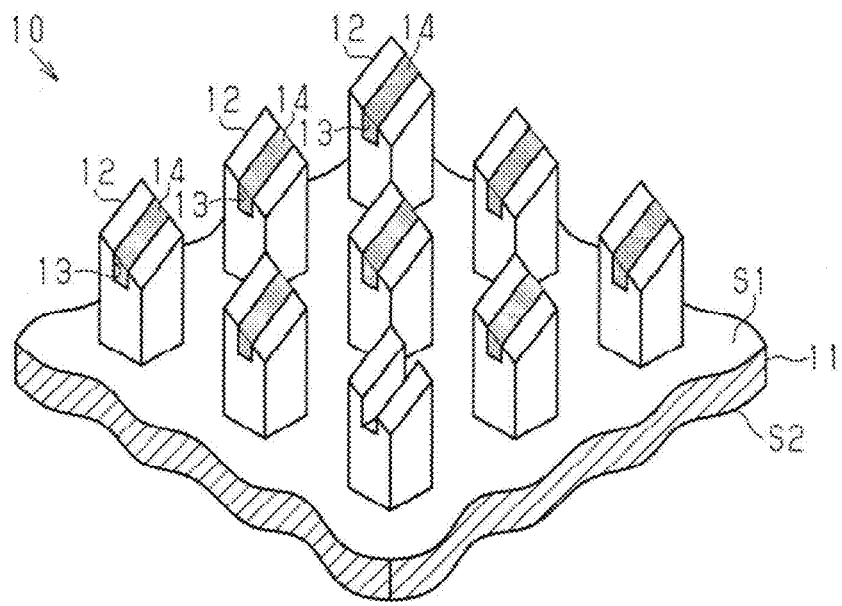
FIG. 3 is a perspective view showing the perspective structure of the microneedle device of the embodiment, which includes a plurality of projections.

As shown in FIG. 3, a plurality of projections 12 may be formed. As long as at least one projection 12 is provided, the number of the projection 12 is not limited. In FIG. 3, for ease of understanding of the shape of the grooves 13 in the projections 12, the projection 12 that is closest to the viewer of FIG. 3 is shown without the freeze-dried drug 14 in the groove 13.

When the microneedle device 10 includes a plurality of projections 12, the projections 12 may be arranged on the surface of the substrate 11 either regularly or irregularly. For example, the projections 12 may be arranged in a lattice pattern or a concentric pattern.

When the microneedle device 10 includes a plurality of projections 12, the grooves 13 of all projections 12 are preferably extend in the same direction. That is, the grooves 13 preferably open in the same direction. Specifically, the grooves 13 of all projections 12 open in the direction perpendicular to the first surface S1 and also open in the same directions along the first surface S1. In other words, all the projections 12 preferably have the same second direction. This facilitates adjusting the wettability of the projection 12 with respect to the liquid drug before freeze-dried so that the wettability can be adjusted for easier injection of the liquid drug into the grooves 13. This increases the accuracy of the loading amounts of the freeze-dried drug 14 in the grooves 13 with respect to the target amount.

When the microneedle device 10 is used, the substrate 11 is pressed onto the skin with the projections 12 facing toward the skin, causing the projections 12 to pierce the skin. This leads to the freeze-dried drug 14 dissolved into water on or in the skin, and the liquefied drug is released out of the grooves 13 and delivered into the body of the subject.

The grooves 13 that receive the freeze-dried drug 14 allow the microneedle device 10 to hold a greater amount of drug than a structure in which the drug is adhered to the surfaces of projections 12.

Other microneedle devices are known that are made of a water-soluble polymeric material, for example, and contain a drug in their projections. When such a microneedle device is used, the projections dissolve while piercing the skin of the subject, delivering the drug into the subject body. Any increase in the amount of drug to be administered by this microneedle device increases the proportion of the drug in the components forming the projections. This reduces the proportion of the component that functions to enhance the mechanical strength, such as a polymeric material, thereby reducing the mechanical strength of the projections. The piercing ability of the projections is therefore reduced. In addition, such a microneedle device is vulnerable to moisture-caused deformation. This tends to lower the piercing ability of the projections during storage.

In contrast, the projections 12 of the present embodiment do not contain a drug and may be made of a material having a high mechanical strength. This allows for an increase in the amount of drug without compromising the piercing ability of the projections 12.

Other microneedle devices are known that include liquid drugs. When such a microneedle device is used, the liquid drug is administered through a through-hole formed in the projection or supplied from an external source when the projections pierce the skin. However, since liquid drugs are not suitable for long-term storage, the microneedle device that includes a liquid drug and is thus stored with the liquid drug inevitably has an earlier expiration date.

In contrast, in the present embodiment, the drug held by the microneedle device 10 is freeze-dried, allowing for a long-term storage of the microneedle device 10 including the drug.

[Microneedle device Manufacturing Method] Referring to FIGS. 4 to 7, a method for manufacturing the microneedle device 10 will now be described.

Figure 4:
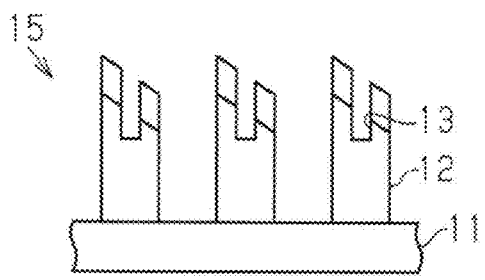
FIG. 4 is a diagram showing a fabricated main body, illustrating a process of manufacturing the microneedle device of the embodiment.

As shown in FIG. 4, a main body 15 including a substrate 11 and projections 12 is first formed.

The main body 15 is preferably made of a biocompatible material. In particular, a biocompatible material that withstands the freeze-dry process of the drug may be used for the main body 15. The possible materials include silicon, metal such as stainless steel, titanium, or manganese, and resins such as medical grade silicone, polylactic acid, polyglycolic acid, polycarbonate, or cyclic olefin copolymer. The main body 15 may contain a water-soluble polymeric material.

The main body 15 may be manufactured using various known techniques. Depending on the material of the main body 15, the main body 15 may be formed by machining, such as dicing or drilling, laser processing, molding such as injection molding, or etching. Such techniques may be used to make the original of the main body 15. The original is used to make a negative mold having projections and depressions that are opposite to those of the original. The negative mold may be made by a plating method or a mold making method using resin. The main body 15 may be duplicated using the negative mold.

Alternatively, the main body 15 may be formed by a transfer molding method using a mold made by machining. More specifically, the main body 15 may be made of resin and formed using a mold through a method such as injection molding, compression molding, or blow molding.

Each groove 13 of the main body 15 of the present embodiment opens in the direction perpendicular to the first surface S1 and directions along the first surface S1 in a continuous manner. This allows the receiving section to be formed easily and with a wider range of processing techniques as compared with a structure in which the receiving section of each projection 12 is a through-hole that opens only in the direction perpendicular to the first surface S1 or a hole that does not extend through the projection 12 and opens only in the direction perpendicular to the first surface S1, for example. When the grooves 13 in the projections 12 open in the same direction, the grooves 13 can be formed continuously in the aligned projections 12 by the dicing method without changing the orientation of the blade. The structure allows the outer shape of the projections 12 and the grooves 13 to be formed by the same processing method. This enhances the production efficiency of the main body 15.

Figure 5:
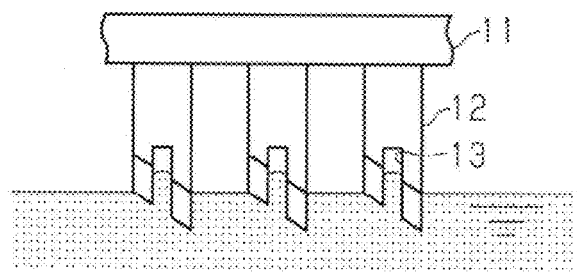
FIG. 5 is a diagram showing an example of a step of loading a drug, illustrating a process of manufacturing the microneedle device of the embodiment.
Figure 6:
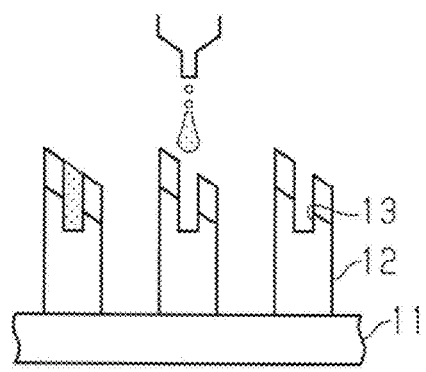
FIG. 6 is a diagram showing an example of a step of loading a drug, illustrating a process of manufacturing the microneedle device of the embodiment.

As shown in FIG. 5, a liquid drug is loaded into the grooves 13 in the projections 12 of the main body 15. The drug may be loaded by dipping the distal ends of the projections 12 into the surface of the stored liquid drug as shown in FIG. 5. The drug is drawn into the grooves 13 by capillary action. Alternatively, as shown in FIG. 6, the drug may be loaded into the grooves 13 by trickling droplets of the drug toward the grooves 13.

The drug may be any type of drug that functions when administered to the skin and is able to be freeze-dried. The drug may be pharmacologically active material, such as vaccines, or a cosmetic composition for providing aesthetic effects.

Each groove 13 of the main body 15 of the present embodiment opens in the direction perpendicular to the first surface S1 and directions along the first surface S1 in a continuous manner. This allows the drug to enter the receiving section from directions other than the direction perpendicular to the first surface S1, unlike a structure in which the receiving section of each projection 12 is a through-hole that opens only in the direction perpendicular to the first surface S1 or a hole that does not extend through the projection 12 and opens only in the direction perpendicular to the first surface S1, for example. The air pressed out of the receiving section by the drug entering the receiving section is released in a direction different from the direction in which the drug enters. This facilitates the entry of the drug into the receiving section.

In addition, the structure of the present embodiment allows the receiving section to have a larger inlet for the drug. The projections 12 are extremely small. The receiving section that opens only in the direction perpendicular to the first surface S1 would be significantly affected by the surface tension of the drug, hindering the entry of the drug into the receiving section. In contrast, the receiving section of the present embodiment has a larger inlet for the drug. The enlarged area of contact between the main body 15 and the drug at the inlet of the receiving section increases the wettability of the main body 15 with respect to the drug, facilitating the entry of the drug into the receiving section.

When the drug is loaded by capillary action, the rising of the drug by capillary action in the structure of the present embodiment depends on factors including the material forming the projections 12, the surface shape of the grooves 13, such as the surface roughness or the periodicity of the processing marks left on the inner surface defining the grooves 13, the properties of the drug, such as viscosity or surface tension, and the width Dm of the grooves 13. Of these factors, the design of the shape of the surface defining the groove 13 and the width Dm of the grooves 13 can be changed in accordance with the material of the projections 12 and the properties of the drug so as to achieve the capillary action. Thus, a wide variety of materials and drugs may be used for the projections 12, expanding the versatility of the present embodiment.

When the drug is loaded by trickling a droplet of the drug, the structure of the present embodiment helps the droplet to be caught by the receiving section on the upper surface S4 of each projection 12 and limits sliding of the droplet off the upper surface S4 as compared with a structure in which the receiving section opens only in the direction perpendicular to the first surface S1. This also facilitates the loading of the drug.

Figure 7:
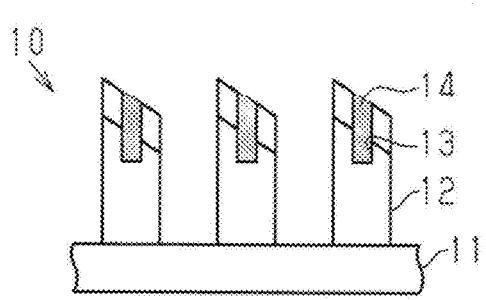
FIG. 7 is a diagram showing the microneedle device after the freeze-drying step, illustrating a process of manufacturing the microneedle device of the embodiment.

As shown in FIG. 7, the drug loaded into the grooves 13 is freeze-dried to obtain a microneedle device 10, in which the freeze-dried drug 14 is received in the grooves 13. Any known freeze-drying method may be used. In the freeze-drying process, the drug is frozen at tens of degrees below zero, and then the water in the frozen drug sublimes under vacuum.

The microneedle device 10 that serves as a drug administration device of the present embodiment has the following advantages.

(1) The groove 13, which serves as the receiving section, receives the drug. This increases the amount of drug the microneedle device 10 can hold as compared with a structure in which the drug is adhered to the surface of the projection 12. Moreover, the microneedle device 10 that includes the freeze-dried drug can be stored for a long time.

Such a microneedle device 10 is manufactured by a method including a step of fabricating the main body 15, which includes the substrate 11 and the projection 12, loading a liquid drug into the receiving section, and freeze-drying the drug loaded into the receiving section.

(2) The groove 13, which serves as the receiving section that receives the freeze-dried drug 14, defines a cavity that is recessed in the direction perpendicular to the first surface S1 toward the substrate 11. The groove 13 also extends in one direction along the first surface S1 so as to open to sections of side surfaces S3 of the projection 12. Such a receiving section facilitates the entry of the liquid drug before freeze-dried, as compared with a receiving section that opens only in the direction perpendicular to the first surface S1. This facilitates the loading of the drug and increases the accuracy of the drug loading amount with respect to the target value.

The structure of the present embodiment allows the receiving section to have a larger capacity and thus receive a greater amount of drug, as compared with a receiving section that opens only in the direction perpendicular to the first surface S1. In addition, a greater amount of drug is exposed out of the surface of the projection 12, increasing the efficiency of freeze-drying and the evenness in freeze-drying of the drug. Furthermore, the greater amount of the drug exposed out of the surface of the projection 12 also allows the freeze-dried drug 14 to efficiently dissolve in water and diffuse into the body when administered. This eliminates the need for dissolving the freeze-dried drug 14 in advance with saline. The drug administration is achieved simply by piercing the subject with the microneedle device 10.

(3) The bottom of the groove 13 is located in the projection 12 at a position separated from the substrate 11.

This increases the mechanical strength of the projection 12 at the base of the projection 12, where stress tends to be concentrated, as compared with a structure in which the groove 13 extends to the substrate 11. Moreover, the freeze-dried drug 14 is concentrated in the part of the projection 12 that goes deeper into the skin than the other part. This ensures that the freeze-dried drug 14 in the groove 13 is delivered into the body.

(4) The groove 13 extends through the projection 12 in a direction along the first surface S1. This helps to increase the capacity of the receiving section and the area of the opening of the receiving section to the peripheral surface of the projection 12. This enhances advantage (2) described above and also facilitates the formation of the groove 13.

(5) The projection 12 has a pointed distal end.

As viewed facing the first surface S1, the tip, which is the apex of the distal end, is located in an edge of the projection 12. Thus, as viewed facing the first surface S1, the groove 13, which is positioned in a region that does not include the tip of the projection 12, is positioned with a higher flexibility. The pointed distal end allows the projection 12 to easily pierce the skin. In addition, the tip of the distal end of the projection 12 is located in an edge of the projection 12, increasing the flexibility in the size, shape, and position of the groove 13.

Further, in the structure described above, the angle of inclination from the tip to the base of the projection 12 is not uniform around the tip of the projection 12. When the drug is loaded into the groove 13 by trickling a droplet of drug, such a structure limits sliding of the droplet off the peripheral surface of the projection 12 as compared with a structure in which the projection is conical in shape and has a uniform inclination angle. This facilitates the loading of the drug into the groove 13.

(6) When a plurality of projections 12 is formed, the grooves 13 of all projections 12 open in the same direction, facilitating the formation of the grooves 13. Specifically, various processing techniques, such as machining or laser processing, may be used to simultaneously form grooves 13 in multiple projections 12 or to successively form a groove 13 in each of the projections 12. This enhances the production efficiency of the main body 15.

[Modifications]

Referring to FIGS. 8 to 18, modifications in the shape of the microneedle device will now be described. Same reference numerals are given to those components that are the same as the corresponding components of the embodiment described above. Such components will not be described in detail.

Figure 8:
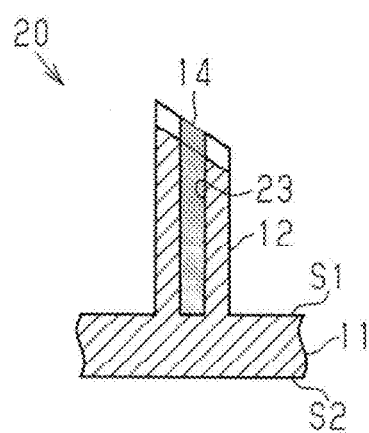
FIG. 8 is a cross-sectional view showing the cross-sectional structure of a microneedle device of a modification.

FIG. 8 shows a microneedle device 20 that includes a groove 23 in place of the groove 13 of the microneedle device 10 of the embodiment. As exemplified by the groove 23 of FIG. 8, the bottom of the groove may be located at the base surface of the projection 12. The groove 23 extends through the projection 12 but does not extend into the substrate 11. The projection 12 of this structure is mechanically weaker than that of the microneedle device 10 of the embodiment but has a larger cavity for receiving the freeze-dried drug 14 and therefore a greater capacity for the freeze-dried drug 14.

Figure 9:
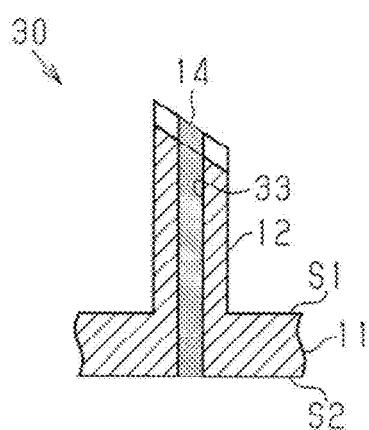
FIG. 9 is a cross-sectional view showing the cross-sectional structure of a microneedle device of a modification.

FIG. 9 shows a microneedle device 30 that includes a channel 33, which serves as a receiving section, in place of the groove 13 of the microneedle device 10 of the embodiment. The channel 33 extends through the substrate 11 and the projection 12 in the extending direction of the projection 12. Except for the extent in the depth direction, the channel 33 is the same as the groove 13 of the embodiment described above.

When the microneedle device 30 is used, liquid including water is preferably injected into the channel 33 through the opening of the channel 33 that opens to the second surface S2 of the substrate 11 while the projection 12 pierces the skin. The freeze-dried drug 14 dissolves in the injected liquid. The liquefied drug then goes out through the opening of the channel 33, which opens to the upper surface S4 of the projection 12, and into the body of the subject.

Such a structure has a larger cavity for receiving the freeze-dried drug 14. Moreover, water is actively supplied to the freeze-dried drug 14 during use of the microneedle device 30, improving the efficiency in drug administration.

Figure 10:
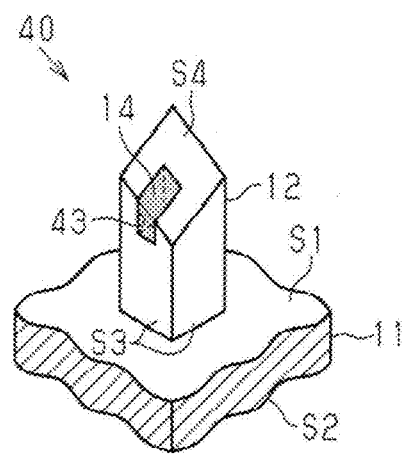
FIG. 10 is a perspective view showing the perspective structure of a microneedle device of a modification.

FIG. 10 shows a microneedle device 40 that includes a groove 43 in place of the groove 13 of the microneedle device 10 of the embodiment. As exemplified by the groove 43 of FIG. 10, the receiving section does not have to extend through the projection 12 in a direction along the first surface S1. The groove 43 still defines a cavity recessed in the direction perpendicular to the first surface S1 toward the substrate 11. The cavity extends continuously in one direction along the first surface S1 so that the groove 43 opens to a section of a side surface S3 of the projection 12. More specifically, the groove 43 opens to the upper surface S4 and a section of a side surface S3 of the projection 12 so as to form a continuous opening.

Figure 11:
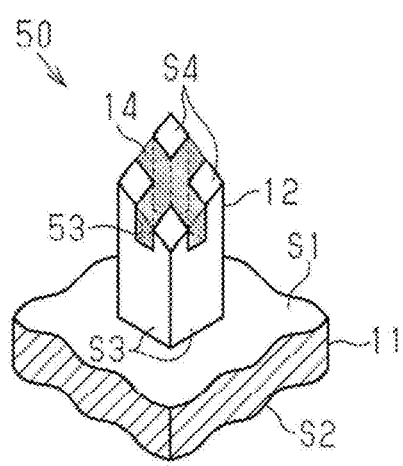
FIG. 11 is a perspective view showing the perspective structure of a microneedle device of a modification.

FIG. 11 shows a microneedle device 50 that includes a groove 53 in place of the groove 13 of the microneedle device 10 of the embodiment. As illustrated in FIG. 11, as long as the receiving section defines a cavity that is recessed toward the substrate 11 in the direction perpendicular to the first surface S1, extends in one direction along the first surface S1, and opens to a side surface S3 of the projection 12, the receiving section may extend in other directions and open to three or more side surfaces S3 of the projection 12. In the example shown in FIG. 11, the groove 53 extends in the direction perpendicular to the first surface S1 and also in directions along the two pairs of opposing sides defining the base surface of the projection 12. In this case, the direction extending along one of the two pairs of opposing sides is the second direction. The groove 53 opens to the upper surface S4 and four sections of the side surfaces S3 of the projection 12 to form a continuous opening. As viewed facing the first surface S1, the groove 53 is cross-shaped.

To increase the ease of formation of the groove and the mechanical strength of the projection 12, the groove preferably opens to the upper surface S4 and two sections in side surfaces S3 of the projection 12 and extends through the projection 12 only in one direction along the first surface S1 as with the case in the embodiment.

Figure 12:
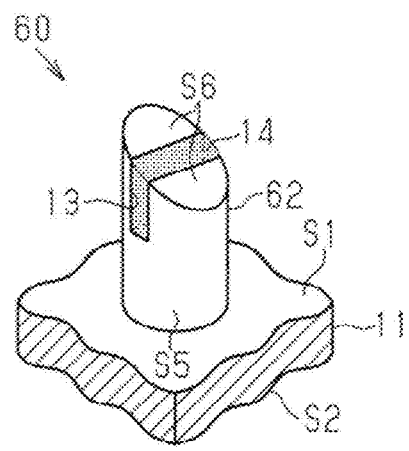
FIG. 12 is a perspective view showing the perspective structure of a microneedle device of a modification.

FIG. 12 shows a microneedle device 60 that includes a projection 62 in place of the projection 12 of the microneedle device 10 of the embodiment. The structure formed by the projection 62 and a freeze-dried drug 14 has the shape of a column that is beveled relative to the extending direction of the column. The projection 62 includes a side surface S5, which serves as a peripheral surface extending perpendicularly from the circular base surface defined in the first surface S1, and an upper surface S6, which is inclined relative to the base surface. The groove 13 defines a cavity extending in the direction perpendicular to the first surface S1 toward the substrate 11. The cavity is recessed continuously in one direction along the first surface S1 so that the groove 13 opens to sections of the side surface S5 of the projection 62. More specifically, the groove 13 opens to the upper surface S6 and two sections of the side surface S5 of the projection 62.

The projection 62 has a pointed distal end. As viewed facing the first surface S1, the tip of the projection 62 is located in an edge of the projection 62.

Figure 13:
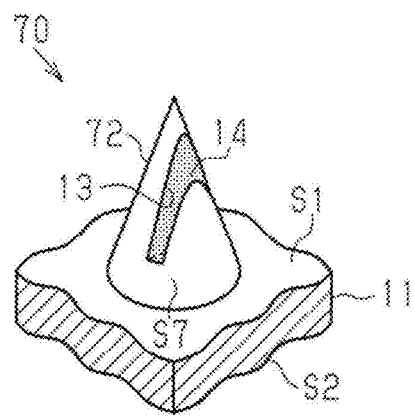
FIG. 13 is a perspective view showing the perspective structure of a microneedle device of a modification.

FIG. 13 shows a microneedle device 70 that includes a projection 72 in place of the projection 12 of the microneedle device 10 of the embodiment. As exemplified by the projection 72 of FIG. 13, the projection may have a pointed distal end, and the tip of the projection may be located in the center of the projection as viewed facing the first surface S1. In the example shown in FIG. 13, the projection 72 is conical, and the groove 13 is offset from the center of the projection 72 as viewed facing the first surface S1. The groove 13 defines a cavity recessed in the direction perpendicular to the first surface S1 toward the substrate 11. The cavity extends continuously in one direction along the first surface S1 so that the groove 13 opens to a section of the peripheral surface S7 of the projection 72. Alternatively, the groove 13 may be located in the center of the projection 72 as viewed facing the first surface S1. The projection 72 may be free of an apex, which serves as the tip of the distal end.

In addition to the examples described above, the projection may have the shape of a quadrangular pyramid or a shape that is free of a pointed distal end, such as the shape of a column or a prism. Further, the projection may have a shape that is formed by combining two or more solids, for example a shape in which a cone is placed on a cylinder. That is, advantage (1) is achieved as long as the projection has a shape that allows piercing of the skin and the receiving section formed in the projection receives a freeze-dried drug.

Figure 14:
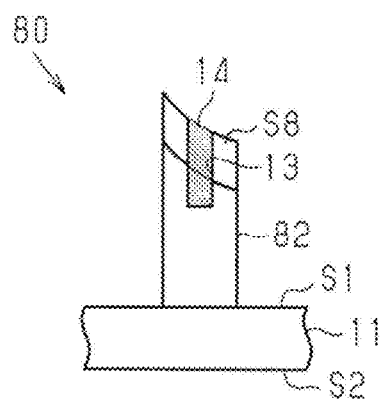
FIG. 14 is a side view showing the side structure of a microneedle device of a modification.

As exemplified by the projection 82 of the microneedle device 80 shown in FIG. 14, the projection may have a curved upper surface S8. Such an upper surface S8 of the projection 82 may be formed by a dicing method using a curved dicing blade.

The shape of the receiving section is not limited to the examples described above, and the receiving section may extend obliquely to the extending direction of the projection. In other words, the first direction is not limited to the direction perpendicular to the first surface S1 and may be any direction that intersects with the first surface S1. In other words, advantage (2) is achieved as long as the receiving section extends away from the substrate 11 in a direction that intersects with the first surface S1 and opens to the distal end in the extending direction and to the peripheral surface extending from the first surface S1. Further, such a receiving section may be shaped such that the size of the groove, which serves as the receiving section, in a plane parallel to the first surface S1 increases or decreases toward the bottom of the groove. In addition, the wall surfaces of the receiving section do not have to be flat.

Figure 15:
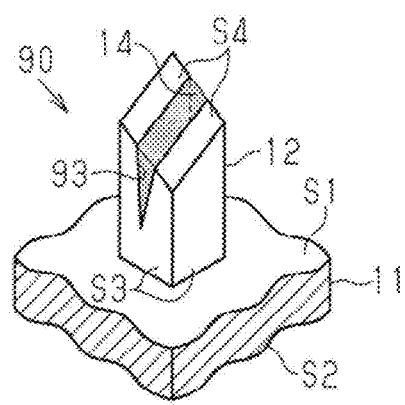
FIG. 15 is a perspective view showing the perspective structure of a microneedle device of a modification.

Specifically, as exemplified by the groove 93 of the microneedle device 90 shown in FIG. 15, the size of the groove in a plane parallel to the first surface S1 may decrease toward the bottom of the groove. In the example shown in FIG. 15, the width Dm of the groove 93 decreases toward the substrate 11 in the direction perpendicular to the first surface S1, which is the first direction. The bottom of the groove 93 forms a line extending in the direction in which the groove 93 extends along the first surface S1, which is the second direction.

Figure 16:
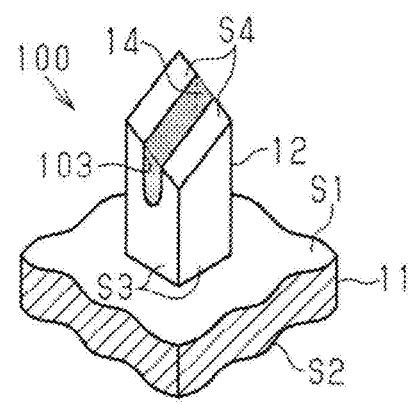
FIG. 16 is a perspective view showing the perspective structure of a microneedle device of a modification.
Figure 17:
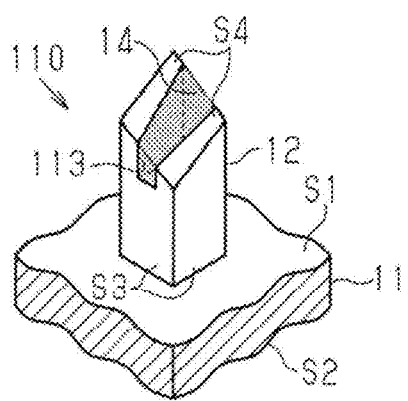
FIG. 17 is a perspective view showing the perspective structure of a microneedle device of a modification.
Figure 18:
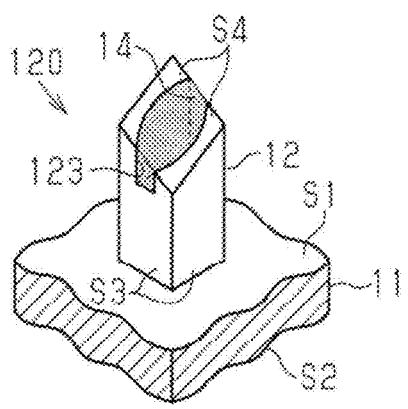
FIG. 18 is a perspective view showing the perspective structure of a microneedle device of a modification.

Alternatively, the bottom surface of the groove may be curved, as exemplified by the groove 103 of the microneedle device 100 shown in FIG. 16. In this case, the bottom of the groove is a part of the bottom surface that is deepest, or closest to the substrate 11.

Further, the width Dm of the groove may vary in the direction in which the groove extends along the first surface S1, that is, the second direction. As exemplified by the groove 113 of the microneedle device 110 shown in FIG. 17, the width Dm of the groove may increase gradually in the second direction from one end of the groove to the other. Alternatively, the width Dm of the groove may be greater at a middle section between the two ends of the groove, as exemplified by the groove 123 of the microneedle device 120 shown in FIG. 18. Further, as with the groove 123 shown in FIG. 18, the inner side surfaces defining the groove may be curved.

Embodiments of the drug administration device are not limited to microneedle devices, and the length Lt of the projection may be tens of mm or greater as long as the section of the projection that receives the freeze-dried drug can pierce the skin. Such a drug administration device may be used with a spacer for adjusting the length of the section of the projection that pierces the skin so that the section of the projection receiving the freeze-dried drug is placed within the skin. Such a structure limits wasting of drug that would otherwise occur if a liquid drug adheres to the substrate 11 when the drug is loaded into the receiving section.

The drug in the receiving section does not have to be freeze-dried as long as it is dried. That is, the drug administration device may include any solid drug. Drying methods that may be used instead of the freeze-dry method include air drying, vacuum drying, and thermal drying, for example. Such a structure still allows the drug administration device to hold a greater amount of drug.

EXAMPLE

A specific example and a comparison example will now be described to illustrate the drug administration device and the method for manufacturing the drug administration device.

Example

[Fabrication of Main Body]

Figure 19A:
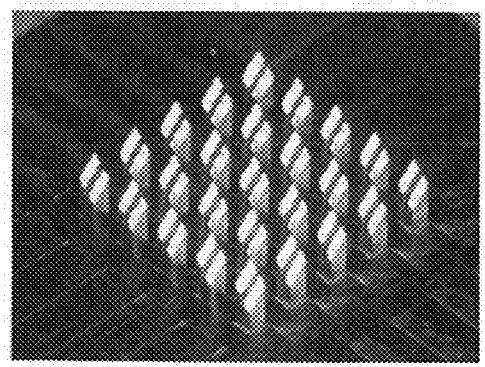
FIG. 19A is a photographed image of the main body of the microneedle device of an example.
Figure 19B:
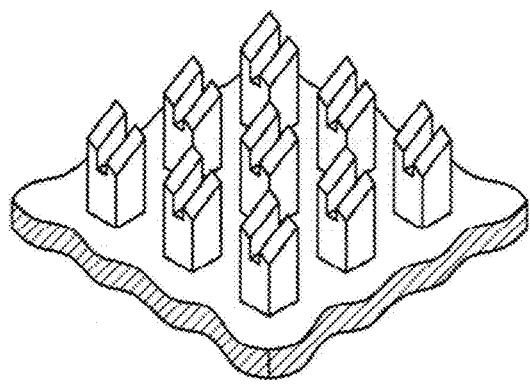
FIG. 19B is a schematic view of the main body in the photographed image of FIG. 19A.

A main body was fabricated using a dicing method. The main body was made of silicon and included 25 projections formed on a substrate. The projections were shaped as shown in FIG. 1 and arranged in a lattice of five rows and five columns. The projections had a length Lt of 1.2 mm and a width Dt of 300 μm. The length Lm between the first surface of the substrate and the bottom of the groove was 400 μm, and the width Dm of the groove was 100 μm. FIG. 19A is a photographed image of the fabricated main body taken using a microscope. FIG. 19B is a schematic view of the main body in the photographed image.

[Drug Formula]

An antigen solution was used in which 30 mg ovalbumin (OVA) (manufactured by Sigma-Aldrich Co. LLC., Grade VI, A-2512-5G), 3000 mg sucrose, and 30 mg Evans blue (EB) (manufactured by Tokyo Chemical Industry Co., Ltd.) were dissolved in 3 ml phosphate buffered saline (PBS). The total amount of the antigen solution of the formula was about 5 mL. The concentration of OVA, which functioned as the antigen, in the antigen solution was therefore about 6 mg/mL.

[Loading of Drug]

By using a pipette, a droplet of the antigen solution was placed on the main body so as to cover the projections and then drawn immediately after the placement. The antigen solution was removed from around the projections but left in the grooves. The antigen solution left on the substrate was drawn with a syringe having a needle. The drug was thus loaded in the grooves.

In the main body, the total capacity of the grooves in the 25 projections of one microneedle device is presumed to be about 0.3 µL. Accordingly, based on the OVA concentration, the amount of OVA loaded into one microneedle device is presumed to be about 1.8 µg.

[Freeze-drying of Drug]

Figure 20A:
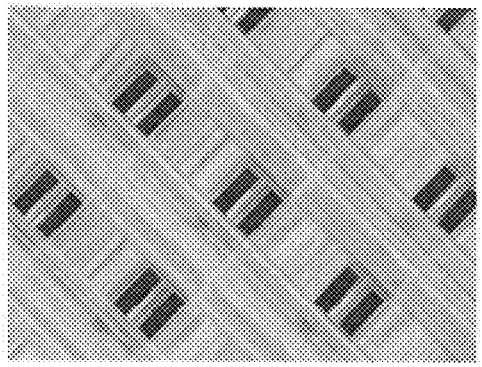
FIG. 20A is a photographed image of projections of the microneedle device of the example before drug loading.
Figure 20B:
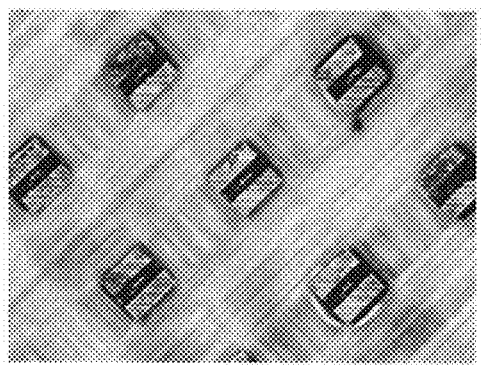
FIG. 20B is a photographed image of the projections of the microneedle device of the example after drug loading.

The main body loaded with the antigen solution was frozen in a freezer at −80° and then transferred to a freeze dryer (manufactured by Tokyo Rikakikai Co., LTD., FREEZE DRYER FD-1). A container with dry ice was used to transfer the main body in a frozen state. The main body then immediately underwent freeze-drying for about half a day. The drug was thus freeze-dried to prepare a microneedle device of the example. FIG. 20A shows a photographed image of the projections taken before the drug is loaded in the grooves. FIG. 20B shows a photographed image of the projections taken after the drug is loaded and freeze-dried in the grooves.

Figure 21A:
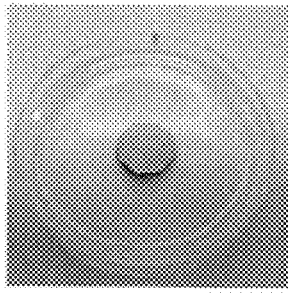
FIGS. 21A to 21C are observation images showing the diffusion process of the drug applied using the microneedle device of the example.
Figure 21B:
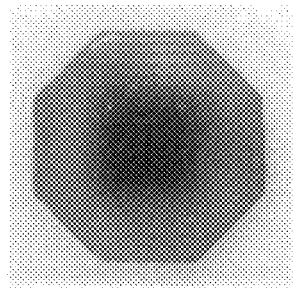
Figure 21C:
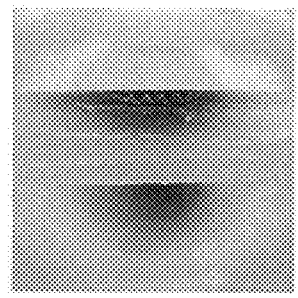

The microneedle device of the example pierced an agar plate to observe the diffusion process of the drug. The observation showed that the microneedle device of the example was capable of drug administration under the simulated condition. FIGS. 21A to 21C show the observation results of drug diffusion after 20 minutes had elapsed since the projections pierced the agar. FIG. 21A is an image showing the entire sample under test. FIG. 21B is an enlarged image of the section of the agar pierced by the microneedle device. FIG. 21C is a cross-sectional image of the section of the agar pierced by the microneedle device.

Comparison Example

[Fabrication of Main Body]

Figure 22A:
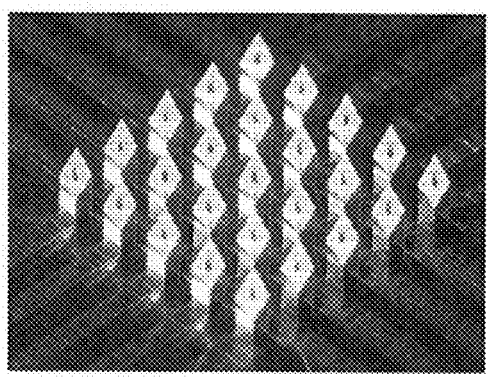
FIG. 22A is a photographed image of the main body of the microneedle device of a comparison example.
Figure 22B:
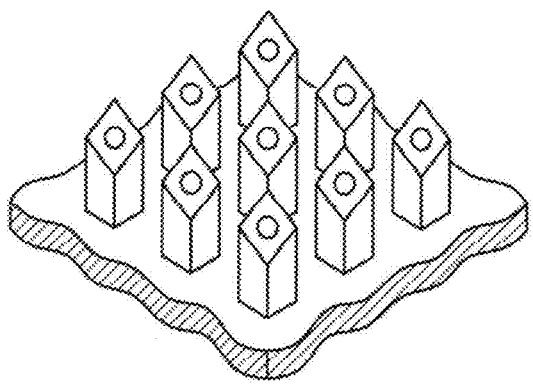
FIG. 22B is a schematic view of the main body in the photographed image of FIG. 22A.

A main body was fabricated that has the same structure as the example except that each projection includes, instead of a groove, a through-hole that opens only in the direction perpendicular to the first surface of the substrate. The through-hole was formed with laser. The projections had a length Lt of 1.2 mm and a width Dt of 300 µm. The diameter of the through-hole was about 150 µm. FIG. 22A is a photographed image of the fabricated main body taken using a microscope. FIG. 22B is a schematic view of the main body in the photographed image.

[Loading of Drug]

An antigen solution that is prepared in the same manner as the example was injected into the through-holes of the main body using a syringe having a needle. The main body was attached to a specific holder. The projections were observed with a stereomicroscope after loading of the antigen solution, and many projections were found lacking the antigen solution or having the antigen solution only in a part of the through-hole. Thus, the antigen solution was loaded into the through-holes by suction through the holes open to the second surface of the substrate. The antigen solution was thus loaded into the through-holes so that the through-holes were substantially filled with the antigen solution. The unnecessary antigen solution left on the substrate was removed by drawing with a pipette or a syringe having a needle or wiped off with paper.

[Freeze-drying of Drug]

Figure 23A:
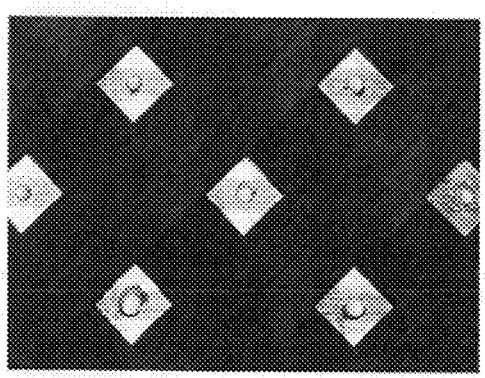
FIG. 23A is a photographed image of projections of the microneedle device of the comparison example before drug loading.
Figure 23B:
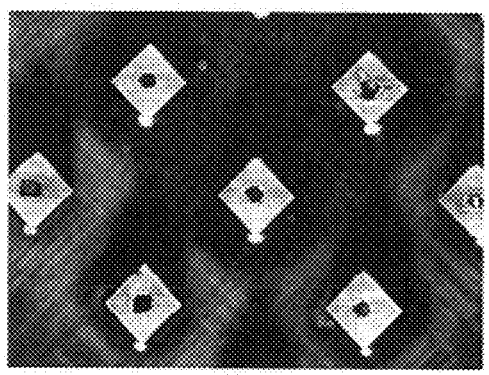
FIG. 23B is a photographed image of the projections of the microneedle device of the comparison example after drug loading.

The drug was freeze-dried under the same condition as the example to prepare a microneedle device of the comparison example. FIG. 23A shows a photographed image of the projections taken before the drug was loaded in the grooves. FIG. 23B shows a photographed image of the projection taken after the drug was loaded and freeze-dried in the grooves.

<Functional Test>

The drug administration performances of the microneedle devices of the example and comparison example were tested.

[Test Method]The drug was administered using the microneedle device of the comparison example in test examples 1 to 4 and administered using the microneedle device of the example in test samples 5 to 8.

The test used 32-week-old male Wistar rats as the drug administration subjects. The hair on the back skin of each anesthetized rat was removed with electrical clippers, and the site for drug administration was further shaved. The skin of the rat was pinched with fingers to form a fold, and a microneedle device, which was attached in advance to an adhesive bandage, was pressed hard between a finger and the skin of the rat so as to pierce the skin. The microneedle device was fixed by winding strapping tape around the body of the rat and left in this state for half a day. After the microneedle device was removed, the skin of the rat was dyed in blue, indicating the freeze-dried antigen solution was dissolved and administered in the skin of the rat. A blood sample was taken from the rat after four weeks had elapsed since the administration, and the antibody titer of OVA-specific immunoglobulin G was measured.

In test examples 9 to 12, an antigen solution was freeze-dried under the same condition as the freeze-drying process of the microneedle device of the example and then dissolved again. The antigen solution was administered to 32-week-old male Wistar rats using a syringe having a needle. A blood sample was taken from each rat after four weeks had elapsed since the administration to measure the antibody titer.

In test examples 13 to 16, an antigen solution that was not freeze-dried was administered to 32-week-old male Wistar rats using a syringe having a needle. A blood sample was taken from each rat after four weeks had elapsed since the administration to measure the antibody titer.

The antigen solution used in test examples 9 to 12, in which the freeze-dried drug was dissolved, and the antigen solution used in test examples 13 to 16, which includes the non-freeze-dried drug, were prepared by diluting OVA with PBS and then adding EB so that the concentration of EB was 1% of the total amount. The solutions were administered to the rats such that the dosage of OVA to each rat was equal to that in test examples 1 to 8.

Test examples 9, 10, 13 and 14 employed intracutaneous administration, and test examples 11, 12, 15 and 16 employed subcutaneous administration.

[Test Results]

Table 1 shows the test results.

TABLE 1

| | Rat No. | Administration method | Dosage | Antibody titer ($2^n$) | Average | Standard error |
|---|---|---|---|---|---|---|
| Test example 1 | 1 | Comparison example (microneedle device with through holes) | <Freeze-dried drug> 1.8 µg of OVA, 180 µg of sucrose, and 1.8 µg of EB/per rat | 13 | 12.3 | 0.41 |
| Test example 2 | 2 | | | 13 | | |
| Test example 3 | 3 | | | 12 | | |
| Test example 4 | 4 | | | 11 | | |

TABLE 1-continued

| | Rat No. | Administration method | Dosage | Antibody titer (2ⁿ) | Average | Standard error |
|---|---|---|---|---|---|---|
| Test example 5 | 5 | Example (microneedle device with grooves) | (presumed amount) | 12 | 12.5 | 0.25 |
| Test example 6 | 6 | | | 13 | | |
| Test example 7 | 7 | | | 13 | | |
| Test example 8 | 8 | | | 12 | | |
| Test example 9 | 9 | Syringe (intracutaneous administration) | <Solution of drug that is freeze-dried and dissolved> 1.8 µg of OVA, 180 µg of sucrose, and 500 µg of EB/50 µL/per rat | 14 | 13.0 | 0.71 |
| Test example 10 | 10 | | | 12 | | |
| Test example 11 | 11 | Syringe (subcutaneous administration) | | 13 | 12.0 | 0.71 |
| Test example 12 | 12 | | | 11 | | |
| Test example 13 | 13 | Syringe (intracutaneous administration) | <Solution> 1.8 µg of OVA, 180 µg of sucrose, and 500 µg of EB/50 vL/per rat | 12 | 12.5 | 0.35 |
| Test example 14 | 14 | | | 13 | | |
| Test example 15 | 15 | Syringe (subcutaneous administration) | | 11 | 11.5 | 0.35 |
| Test example 16 | 16 | | | 12 | | |

Table 1 shows that the administration of the freeze-dried drug using the microneedle device achieved equivalent effects as the administration of the freeze-dried or non-freeze-dried drug using the syringe. In addition, the tests showed that the microneedle device of the example allowed for easier loading of the drug before being freeze-dried than the comparison example. Furthermore, the test demonstrated that the microneedle device of the example, which held a greater amount of drug, had a good piercing ability.

DESCRIPTION OF THE REFERENCE NUMERALS

10, 20, 30, 40, 50, 60, 70, 80, 90, 100, 110, 120: microneedle device, 11: substrate, 12, 62, 72, 82: projection, 13, 23, 43, 53, 93, 103, 113, 123: groove, 33: channel, 14: freeze-dried drug, 15: main body, S1: first surface, S2: second surface, S3, S5: side surface, S4, S6, S8: upper surface, S7: peripheral surface

The invention claimed is:

1. A drug administration device comprising:
a substrate having a first surface;
a projection extending from the first surface and including a peripheral surface; and
a solid drug, wherein
the projection includes a receiving section,
the receiving section defines a cavity recessed in a first direction that intersects with the first surface toward the substrate and extends in a second direction that extends along the first surface to open to a section of the peripheral surface of the projection,
the projection includes a pointed distal end having an apex,
the projection includes a quadrilateral upper surface inclined relative to the first surface, the apex of the projection being positioned on the quadrilateral upper surface,
as viewed facing the first surface, the apex is located on an edge of the projection,
the receiving section extends through the projection in the second direction and from a first side of the quadrilateral upper surface to a second side of the quadrilateral upper surface that is opposite to the first side, the first side extending from the apex of the projection, and
the drug is received in the receiving section.

2. The drug administration device according to claim 1, wherein the drug is a freeze-dried drug.

3. The drug administration device according to claim 1, wherein
the receiving section is a groove having a bottom, and
the bottom of the groove is located at a position separated from the substrate in the first direction.

4. The drug administration device according to claim 1, wherein
the projection is one of a plurality of projections, and
all of the projections have the same second direction.

5. A method for manufacturing a drug administration device according to claim 1, comprising:
a first step of fabricating a main body, wherein the main body includes the substrate and the projection;
a second step of loading a liquid drug into the receiving section; and
a third step of drying the drug loaded in the receiving section.

6. The method for manufacturing a drug administration device according to claim 5, wherein the third step includes freeze-drying the drug.

* * * * *